United States Patent
Niedospial, Jr. et al.

[11] Patent Number: 5,984,912
[45] Date of Patent: Nov. 16, 1999

[54] COLLAPSIBLE MEDICAL BAG FOR THE CONTAINMENT AND DELIVERY OF DIAGNOSTIC CONTRAST MEDIA AND PARENTERAL DRUG FORMULATIONS

[75] Inventors: John J. Niedospial, Jr., Burlington; Irene K. Ropiak, Somerset; Charles R. Quirico, warren, all of N.J.

[73] Assignee: Brocco Diagnostics, Inc., Princeton, N.J.

[21] Appl. No.: 08/900,738

[22] Filed: Jul. 25, 1997

[51] Int. Cl.$^6$ ................................................. A61B 19/00
[52] U.S. Cl. ........................................... 604/408; 604/408
[58] Field of Search ........................ 604/403, 408, 604/411, 412, 262, 82, 85; 128/DIG. 24; 383/105, 106, 109, 901; 206/438

[56] References Cited

U.S. PATENT DOCUMENTS

| | | |
|---|---|---|
| Re. 32,065 | 1/1986 | Ralston et al. . |
| 2,847,007 | 8/1958 | Fox . |
| 4,088,166 | 5/1978 | Miller . |
| 4,140,162 | 2/1979 | Gajewski et al. . |
| 4,160,473 | 7/1979 | Winchell . |
| 4,657,540 | 4/1987 | Iwamoto et al. ................ 604/408 |
| 4,892,537 | 1/1990 | Carmen et al. . |
| 4,976,707 | 12/1990 | Bodicky et al. . |
| 5,006,118 | 4/1991 | Yule ................................ 604/408 |
| 5,088,994 | 2/1992 | Porat . |
| 5,391,163 | 2/1995 | Christine et al. ............... 604/408 |
| 5,395,365 | 3/1995 | Weiler et al. . |
| 5,423,794 | 6/1995 | Adolf et al. . |
| 5,632,738 | 5/1997 | Sumi et al. ..................... 604/408 |
| 5,649,907 | 7/1997 | Mori et al. ....................... 604/85 |
| 5,681,627 | 10/1997 | Mueller .......................... 604/408 |
| 5,738,671 | 4/1998 | Niedosial, Jr. et al. ......... 604/408 |

*Primary Examiner*—Corrine McDermott
*Assistant Examiner*—David J. Cho
*Attorney, Agent, or Firm*—Imre Balogh

[57] ABSTRACT

Collapsible, non-vented medical container for the containment and delivery of parenteral solutions, the container having (a) first and second collapsibly thin polymeric sheets of a generally parabolic configuration superimposed and sealed together at their periphery to form
  (1) a reservoir;
  (2) a non-collapsible top portion;
  (3) a on-collapsible bottom portion;
  (4) parabolic side portions; and
(b) an access member or port.

3 Claims, 1 Drawing Sheet

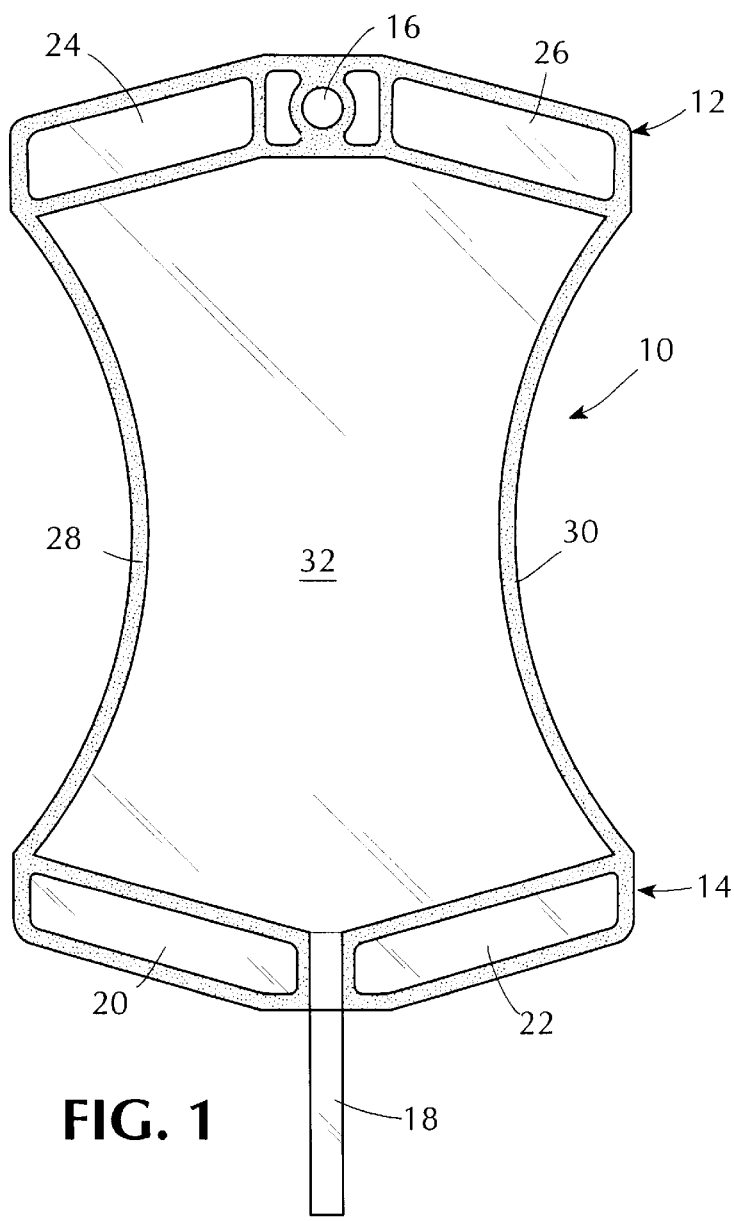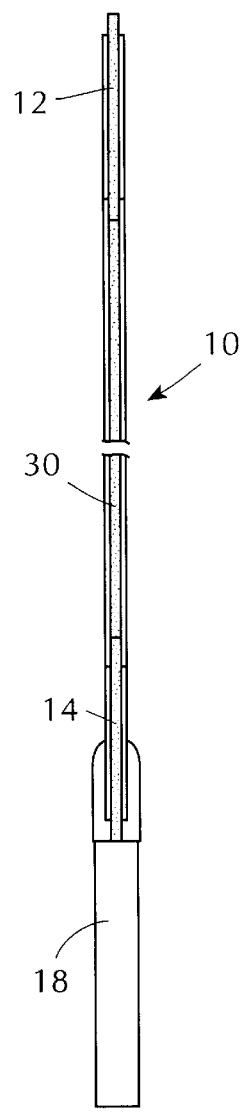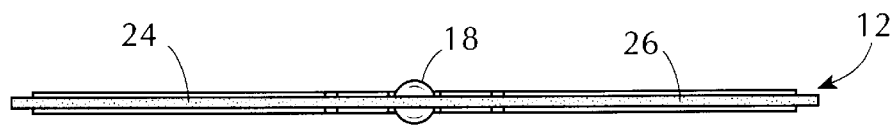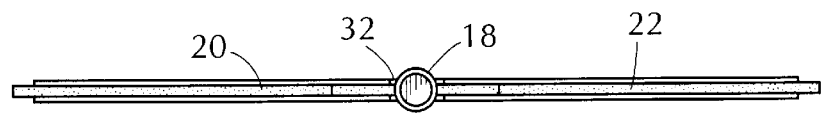

COLLAPSIBLE MEDICAL BAG FOR THE CONTAINMENT AND DELIVERY OF DIAGNOSTIC CONTRAST MEDIA AND PARENTERAL DRUG FORMULATIONS

BACKGROUND OF THE INVENTION

1. Field of the Invention

This invention relates to collapsible medical bags having a generally parabolic shape for the containment of diagnostic media and parenteral drug formulations and delivery thereof in a uniform, steady manner without retaining liquid droplets on their inside walls.

2. Reported Developments

Prior to the discovery and development of polymeric materials, parenteral liquids have been supplied to hospitals exclusively in glass bottles. The disadvantages of glass bottles, such as cost, shipping, storage and disposal, prompted the prior art to provide flexible, sterilizable containers in the forms of bags and bottles for the containment and delivery of parenteral solutions, such as diagnostic contrast media, nutritional and drug formulations. Such containers typically comprise: a flexible plastic sheet formed into a pouch, bag or bottle shape filled with a solution inside therein in a sterile environment; and one or more ports to fill and/or access the solution. Flexible tubing is also provided one end of which is connectable to a port on the container, and the other end connectable to a syringe or catheter pre-inserted into the site of delivery on the patient. Control means are also usually included with the tubing, such as valves and clamps for initiating, controlling and terminating the flow of the liquid to the delivery site. The container, tubing and control means are sterile packaged ready for use.

One of the requirements to be satisfied in flexible containers for delivering parenteral solutions to patients is that by their construction and design they deliver their total contents in a uniform, steady manner and without retaining liquid drops on their walls. By meeting such requirement the medical practitioner can determine the amount of parenteral solution delivered from the container to the patient. The prior art has addressed this requirement, as shown for example in U.S. Pat. No. 4,892,537, which discloses a bag having substantially parallel major sides or edges and converging minor sides which meet at a point forming an obtuse angle of at least 110°. The converging edges are designed to guide the filled bag contents in a substantially unobstructed manner in a funnel-like fashion to an exit port.

U.S. Pat. No. 4,088,166 also addresses the problem of incomplete and non-uniform collapse of parenteral solution containers. The incomplete collapse is attributed to the stiffness of the thin-walled polypropylene container which tends to resist collapse to such a degree that the moderate suction pressure exerted on the container by weight of the parenteral solution is insufficient to cause its complete collapse. The non-uniform collapse, on the other hand, is attributed to the observed facts that on some occasions, the bags collapse along the long axis of their cross section, while on other occasions they tend to collapse along both the short axis of the cross-section as well as the long axis. As a result, the medical practitioners cannot determine exactly how much parenteral solution has been delivered out from the container. In order to solve the problem of incomplete and non-uniform delivery, the patentee incorporates gusset portions in the body portion of the container adjacent the shoulder portion. The gusset portions include lines of flexing weakness to facilitate the collapse of the container adjacent the shoulder portion as the contents thereof are withdrawn. The gussets said to facilitate both the lateral and longitudinal collapse of the container as it is emptied.

Medical practitioners have also observed fluid "hold up", i.e., when drops of parenteral solutions tend to remain on the internal walls of the flexible container as the solution is being delivered to the site of administration. The moderate suction pressure exerted on the walls of the container is insufficient to overcome the force existing between the drops of liquid and the walls of the container. Often, as the container is being drained, the emptied portion of the parallel walls adhere to each other further trapping drops of the liquid. As a consequence, the prescribed amount of parenteral solution is not delivered to the patient. Such delivery, especially in traumatic circumstances where a precise amount of a drug must be delivered into the patient, can make the difference between life and death of the patient.

The present invention addresses the problems associated with the lack of complete delivery of content, caused by incomplete and non-uniform collapse of the container during administration of the parenteral solution resulting in hold up of droplets of the solution on the walls of the container.

SUMMARY OF THE INVENTION

The present invention addresses the problem of incomplete and non-uniform delivery of parenteral solutions, such as diagnostic media and drug formulations by providing a uniformly collapsible non-vented medical bag comprising:

(a) first and second collapsibly thin polymeric sheets having a generally parabolic side configuration superimposed and sealed together at their periphery to form
  1. an interior reservoir,
  2. a non-collapsible top portion;
  3. a non-collapsible bottom portion, and
  4. parabolic side portions and
(b) an access member
  wherein said top portion comprises:
    a center area where the polymeric sheets sealed together form a hole for suspending the bag during delivery of its content;
    two symmetrically positioned rectangular areas extending outwardly from the center of the bag and sealed at their periphery to render said top portion less flexible than the polymeric sheets which form the interior reservoir;
  said bottom portion comprises:
    two symmetrically positioned rectangular areas extending outwardly from the center of the bag and sealed at their periphery to render said bottom portion less flexible than the polymeric sheets which form the interior reservoir, said interior reservoir at its bottom portion terminates in a first angle and a second angle of from about 5° to about 45° each from the center thereof and relative to a horizontal plane crossing the center of said bottom portion;
  said parabolic side portions are designed to flex inwardly when the medical bag is filled with a parenteral solution;
  said access member located in the center of the bottom portion where said first angle and said second angle meet.

BRIEF DESCRIPTION OF THE DRAWING

FIG. 1 is a plan view of the collapsible medical bag of the present invention;

FIG. 2 is a side plan view thereof;

FIG. 3 is a top plan view thereof; and

FIG. 4 is a bottom plan view thereof.

DETAILED DESCRIPTION OF THE INVENTION

The present invention provides a collapsible medical container, in the shape of a bag or pouch, for the containment and delivery of diagnostic contrast media and parenteral drug formulations. In the drawings the reference character 10 indicates the medical bag or pouch which comprises two superimposed sheets of suitable length and width made of thin, pliable, collapsible materials, such as polymeric materials including polyethylene, polypropylene and preferably thermoplastic materials. The superimposed sheets forming the medical bag or pouch are preferably made of transparent materials so as to allow observation of the amount of its content during the filling operation and delivery thereof to the patient. Each of the superimposed transparent sheets is preferably formed of multilayers of laminated thin films at least one of which constitutes a barrier which is impervious to atmospheric gases, moisture and bacteria. The superimposed sheets are preferably flat welded to each other at their periphery so as to form the bag or pouch whose volume is zero prior to being filled with a diagnostic agent or a parenteral solution. When the bag or pouch is filled, it assumes the shape of a small cushion having a parabolic configuration on each side thereof. Depending on the volume intended for delivery to the patient the internal volume capacity of the bag may be from about 50 to about 1000 ml or more. When the internal volume capacity is low, such as 50 to 100 ml, the configuration of the bag or pouch prior to being filled is as shown in FIG. 1; subsequent to filing, the configuration of the bag or pouch approximates the shape of an hourglass having two symmetrical chambers wherein the two chambers are connected by a narrow channel.

Reference is now being made to the parts of the medical bag or pouch 10.

First and second collapsibly thin polymeric sheets having a generally parabolic side configuration are superimposed on each other and sealed at their periphery 28 and 30 to form a generally parabolic shaped interior reservoir 32 for the containment of diagnostic media and parenteral formulations. The medical bag or pouch 10 further comprises a noncollapsible top portion 12 and a non-collapsible bottom portion 14.

Top portion 12 of the medical bag or pouch 10 comprises: a center area where the polymeric sheets are sealed together to form a hole 16 for suspending the medical bag or pouch 10 during delivery of its content; two symmetrically positioned rectangular areas 24 and 26 extending outwardly from hole 16 and sealed at their periphery to render the top portion 12 less flexible than the polymeric sheets which form the interior reservoir 32.

Bottom portion 14 of the medical bag or pouch 10 comprises two symmetrically positioned rectangular areas 20 and 22 extending outwardly from the center of the medical bag or pouch where access member 18 is located and sealed at their periphery to render the bottom portion 14 less flexible than the polymeric sheets which form the interior reservoir 32.

The interior reservoir 32 at its bottom portion terminates in a first angle and a second angle of from about 5° to about 45°, preferably from 10° to 30° and most preferably from 10° to 20° each from the center thereof and relative to a horizontal plane crossing the center of the bottom portion to direct and facilitate the flow of content contained in the medical bag or pouch towards the access member 18.

Access member of access port 18 is located at the center of bottom portion of the medical bag or pouch 10 sealed between the first sheet and second sheet. It serves for both the filling of the medical bag or pouch with diagnostic media or parenteral formulations and for delivery thereof. It is important that the top, distal end of the access member contacting the medical liquid is located flush or just below a horizontal plan crossing the center of the bottom portion of interior reservoir so that all the liquid content can be drained from the medical bag or pouch.

Parabolic side portions 28 and 30 are designed to flex inwardly when the medical bag or pouch 10 is filled with the liquid content. Prior to filling, the medical bag or pouch is flat as shown in FIGS. 1–4 allowing economical handling, storage and shipping. Upon filling, the medical bag or pouch 10 assumes a configuration which approximates the configuration of an hourglass: the parabolic side portions move towards each other narrowing into a channel-like portion at their midportions. The internal configurations of reservoir 32 is as follows.

The center portion assumes a circular shape. Moving gradually towards top portion 12 and bottom portion 14, the circular shape gradually changes or tapers to elliptical. At the extreme top and bottom portions of the medical bag or pouch 10 the internal reservoir assumes a generally flat configuration resembling the configuration of the medical bag or pouch prior to filling. The reason for maintaining this configuration is that top portion 12 and bottom portion 14 are semi-rigid or at least much less flexible than the pliable, thin sheets forming the reservoir.

When the content of the medical bag or pouch is being delivered the reversal of the above-described change of configuration occurs: The center portion gradually loses its circular shape and assumes an elliptical shape. Above and below the center portion the change from existing elliptical to flat occurs faster than the change from circular to elliptical. This keeps the superimposed walls of the reservoir 32 from sticking together thereby preventing the liquid droplets "hold up" on the walls. As such, the total content of the medical bag or pouch is delivered to the patient. The configuration also provides a uniform and steady delivery without collapse of the walls.

Materials of Construction

The medical bag or pouch of the present invention is made of known polymeric materials having properties which make them suitable for sterile delivery of parenteral liquids. The sheets for forming the walls of the container are monolayer, preferably multilayer, sheets and characterized by heat resistance, gloss, strength, flexibility, and chemical inertness. Preferably the sheets are transparent or at least translucent enabling visual inspection of the contents at all times during delivery of content from the container to the patient. The container must be sterilizable by dry heat, steam heat, irridiation (gamma), along with its content. At least one layer of the sheet provides a barrier to atmospheric gases and to steam. Preferably, the internal surface of the medical bag or pouch in contact with the parenteral solution should be impervious to gases and steam. The interior layer in contact with the parenteral solution must not contain any toxic agents or even plasticizers which could leach out and contaminate the solution. The sheet may be made, for example, from polyvinyl chloride sandwiched between two polyethylene or polyvinylacetate layers. The polyvinyl chloride constitutes the impervious barrier. Further layers may be added to the face or back of the sheet, if desired, such as a polyolefin, preferably, polyethylene. Polyvinyl chloride is also suitable for the construction of the sheet and is well-accepted by the prior art for use in containers for medical fluid collection and delivery. Typical properties of polyvinyl chloride films include: a thickness of about 380 micron; a tensile strength of about 240 kg/cm$^2$; a moisture vapor transmission rate of about 14–20 (g/m/day at 38° C., 100% RH); and an oxygen barrier of 650 (cc/m$^2$/day at 23° C., 0% RH, bar. CRYOVAC® sterlizable medical files (W. R. Grace and Co.) are especially suitable to construct the sheets used in the present invention. The films may comprise a polyethylene layer sandwiched between polyester outer layers sealed together by a modified propylene copolymer. Typical properties of the film include: a thickness of about 190 micron; a tensile strength of about 250 kg/cm$^2$; a moisture vapor transmission rate of 5 (g/m$^2$/day at 38° C., 100% RH); and an oxygen barrier of about 1500 (cc/m$^2$/day at 23° C., 0% RH, bar).

Other preferred polymeric films or sheets for constructing the medical bag or pouch of the present invention include: copolyester ether monolayer or multilayer films, such as polycyclohexanedimethylcyclohexane dicarboxylate elastomer made by Eastman Chem. Co.; and ethyl vinyl acetate made by Stedim, Inc. It is important that the fluid contacting layer of the multilayer sheet contain no plasticizer which may contaminate the fluid content of the container. Preferably, no plasticizer should be used at all on any of the multilayers to form the collapsible container of the present invention. comprise three concentric layers of polymeric materials: a polyolefin layer is sandwiched between an outer layer of modified propylene copolymer and an inner layer of ethylene vinyl acetate or polyvinyl chloride.

Process of Making the Medical Bag or Pouch

The medical bag or pouch is made of two sheets of polymeric materials flat welded together on four sides so as to define between the two sheets and the four welded sides a reservoir. The volume of the container is zero before it is filled and typically has an internal volume capacity of from about 50 to about 1,000 ml when it is filled with a medical fluid, such as a parenteral solution. The access member or port 18 is sealed by the same welding process used to seal the two superimposed layers of sheets together at the center of the medical bag or pouch. Upon completion of the welding process the container is filled through the access member or port with the desired medical fluid. Alternatively, the container may be sealed by heat welding at its four edges except at its center portion and filled with the desired medical fluid prior to sealing access member or port 18 between the superimposed sheets. With either process, the medical bag or pouch of the present invention, when filled with the desired medical fluid, provides for instant delivery requiring no assembly of the medical bag or pouch and access member or port.

In the process of delivering the medical fluid to a patient, the container 10 is suspended via hole 16, and IV tubing or similar means is engaged with the proximal end of the access member or port. One way luer slip stopcock assembly on the tubing is turned to open position thereby starting the flow of medical fluid from the medical bag or pouch through the tubing to the site of delivery on the patient. Venting is not provided and is not required to replace the drained medical fluid in the medical bag or pouch since the thin sheets of the reservoir will collapse creating no suction or vacuum. The liquid flow is steady and continuous. If discontinuation of fluid flow is desired, the one-way luer stopcock assembly is turned to the stop position.

The present invention was tested against other medical containers of various configurations and was found to be functioning surprisingly well without allowing hold up of droplets on the walls of the medical bag or pouch or uneven collapse of the walls creating a negative pressure which causes unsteady and incomplete delivery of the content.

Various modifications of the disclosed embodiment will become apparent. This invention is intended to include such modifications to be limited only by the scope of the claims.

What is claimed is:

1. A prefilled, non-vented medical container having a parenteral solution therein comprising:
  (a) first and second collapsibly thin polymeric sheets superimposed and sealed together at their periphery to form
    (1) an hourglass-shaped reservoir consisting of two symmetrical chambers with a narrow connecting channel therebetween,
    (2) a non-collapsible top portion comprising a center area where said first and second collapsibly thin polymeric sheets sealed together form a hole for suspending said prefilled, non-vented medical container and two symmetrically positioned rectangular areas extending outwardly from the center area of the top portion sealed at their periphery to render said non-collapsible top portion less flexible than the collapsibly thin polymeric sheets which form said hourglass-shaped reservoir,
    (3) a non-collapsible bottom portion comprising a center area designed to receive an access member, and two symmetrically positioned rectangular areas extending outwardly from said center area sealed at their periphery to render said non-collapsible bottom portion less flexible than the collapsibly thin polymeric sheets which form said hourglas-shaped reservoir, and
  (b) an access member sealed into said center area of said non-collapsible bottom portion.

2. The collapsible, non-vented medical container of claim 1 wherein said parenteral solution is a diagnostic agent.

3. The collapsible, non-vented medical container of claim 1 wherein said parenteral solution is a drug formulation.

* * * * *